United States Patent [19]

Varma et al.

[11] Patent Number: 4,695,586
[45] Date of Patent: Sep. 22, 1987

[54] 7-OXABICYCLO(2.2.1)HEPTANE-BASED DERIVATIVES USEFUL AS ANTIINFLAMMATORY, ANTIASTHMA AND ANTIPSORATIC AGENTS

[75] Inventors: Ravi K. Varma, Belle Mead; Sam T. Chao, East Windsor; Eric M. Gordon, Pennington, all of N.J.

[73] Assignee: E. R. Squibb & Sons, Inc., Princeton, N.J.

[21] Appl. No.: 910,597

[22] Filed: Sep. 23, 1986

[51] Int. Cl.[4] .................. A61K 31/557; C07D 307/00
[52] U.S. Cl. ..................................... 514/469; 549/463
[58] Field of Search ......................... 549/463; 514/469

[56] References Cited

U.S. PATENT DOCUMENTS 4,143,054  3/1979  Sprague ............................. 549/463
4,254,044  3/1981  Sprague ............................. 549/463
4,582,854  4/1986  Hall et al. .......................... 549/463

FOREIGN PATENT DOCUMENTS 0083204  12/1982  European Pat. Off. .

Primary Examiner—Henry R. Jiles
Assistant Examiner—Bernard I. Dentz
Attorney, Agent, or Firm—L. S. Levinson; T. R. Furman, Jr.

[57] ABSTRACT

7-Oxabicyclo(2.2.1)heptane-based N-hydroxy-N-alkyl (or aryl) ureas, carbamic acids and carbamothioic acids are disclosed having the general formula

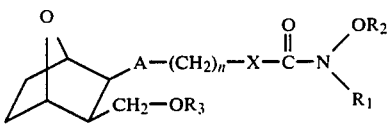

wherein $R_1$ is hydrogen, lower alkyl, alkenyl, aryl or aralkyl; $R_2$ is hydrogen, lower alkyl, aralkyl, alkanoyl or aroyl; $R_3$ is lower alkyl, alkenyl or alkynyl; A is $-CH_2-CH=CH-$ or a single bond; X is oxygen, sulfur or NH; n is an integer from 1 to 8; and all stereoisomers thereof.

These new compounds have been found to simultaneously inhibit the enzymes arachidonic acid cyclooxygenase and arachidonic acid 5-lipoxygenase and are therefore useful as antiinflammatory, antiasthma and antipsoriatic agents.

12 Claims, No Drawings

7-OXABICYCLO(2.2.1)HEPTANE-BASED DERIVATIVES USEFUL AS ANTIINFLAMMATORY, ANTIASTHMA AND ANTIPSORATIC AGENTS

FIELD OF THE INVENTION

The present invention relates to 7-oxabicyclo(2.2.1-)heptane-based derivatives and more particularly concerns such derivatives which simultaneously inhibit the enzymes arachidonic acid cyclooxygenase and arachidonic acid 5-lipoxygenase and as such are useful, for example, as antiinflammatory, antiasthma and antipsoriatic agents.

BACKGROUND OF THE INVENTION

In European patent application Ser. No. 823068689 to Wakatsuka 2-amino-4-phenylthio-phenol compounds and their analogs are disclosed having utility as inhibitors of both 5-lipoxygenase and cyclooxygenase.

In a copending application entitled "7-OXABICYCLO(2.2.1)HEPTANE HYDROXAMIC ACID DERIVATIVES USEFUL AS 'DUAL INHIBITORS'" filed on August 26, 1986, and now U.S. Pat. No. 4,672,075, new 7-oxabicyclo(2.2.1)heptane hydroxamic acid derivatives useful as inhibitors of arachidonic acid 5-lipoxygenase and arachidonic acid cyclooxygenase are provided having the general formula

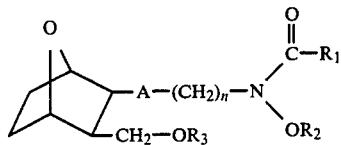

are disclosed wherein $R_1$ is hydrogen, lower alkyl, aryl, aralkyl or alkenyl; $R_2$ is hydrogen, lower alkyl, alkanoyl or aroyl; $R_3$ is lower alkyl, alkenyl or alkynyl; A is $-CH_2-CH=CH-$ or a single bond; and n is an integer from 0 to 9, with the proviso that when A is a single bond, n is an integer from 1 to 9; and including all steroisomers and pharmaceutically acceptable salts thereof.

New compounds effective as "dual inhibitors", i.e. inhibitors of both the arachidonic acid enzymes 5-lipoxygenase and cyclooxygenase, would be a useful addition to the art.

SUMMARY OF THE INVENTION

In accordance with the present invention new 7-oxabicyclo(2.2.1)heptane-based N-hydroxy-N alkyl (or aryl) ureas, carbamic acids and carbamothioic acids useful as inhibitors of arachidonic acid 5-lipoxygenase and arachidonic acid cyclooxygenase are provided.

These new compounds have the general formula

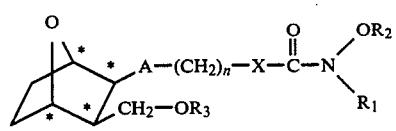

wherein $R_1$ is hydrogen, lower alkyl, alkenyl, aryl or aralkyl; $R_2$ is hydrogen, lower alkyl, aralkyl, alkanoyl or aroyl; $R_3$ is lower alkyl, alkenyl or alkynyl; A is $-CH_2-CH=CH-$ or a single bond; X is oxygen, sulfur or NH; n is an integer from 1 to 8; and all stereoisomers thereof.

DETAILED DESCRIPTION OF THE INVENTION

The derivatives of the present invention may form salts with alkali metals, such as lithium, sodium or potassium. In addition, the compounds of formula I will form salts with dicyclohexylamine or other amines as well as with tris(hydroxymethyl)aminomethane, glucamine and other amines as set out in U.S. Pat. No. 4,294,759.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an aralkyl substituent, a haloaryl substituent, a cycloalkyl substituent, an alkylcycloalkyl substituent, hydroxy, an alkylamino or dialkylamino substituent, an alkanoylamino substituent, an arylcarbonylamino substituent, a nitro substituent, a cyano substituent, a thiol substituent or an alkylthio substituent.

The term "cycloalkyl" employed herein by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, which groups are substituted with the same, or a different cycloalkyl.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substitutent on either the phenyl or naphthyl may be 1 or 2 lower alkyl groups, 1 or 2 halogens (Cl, Br or F), 1 or 2 lower alkoxy groups, 1 or 2 hydroxyl groups, 1 or 2 alkylamino or dialkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" as employed herein by itself or as part of another group includes an unsaturated hydrocarbon group having from 2 to 8 carbons and a single carbon-carbon double bond, such as ethenyl, 1-propenyl, 2-propenyl, 1-butenyl, 2-butenyl, 3-butenyl and the like.

The term "lower alkynyl" or "alkynyl" as employed herein by itself or as part of another group includes an unsaturated hydrocarbon group having from 2 to 8 carbons and a single carbon-carbon triple bond, such as ethynyl, 1-propynyl, 1-butynyl, 2-butynyl, and the like.

The term "alkanoyl" as used herein by itself or as part of another group refers to an alkyl carbonyl group.

The term "aroyl" as used herein by itself or as part of another group refers to an aryl carbonyl group.

The term "halogen" or "halo" as used herein refers to chlorine, bromine, fluorine or iodine with chlorine being preferred.

Preferred are those compounds of the invention wherein $R_1$ is lower alkyl, $R_2$ is H, $R_3$ is n-hexyl, A is $CH_2$—CH=CH and n=2.

The various compounds of the invention may be prepared as described below.

To make the N-hydroxy-N-alkyl (aryl) ureas of formula I, i.e. where X is NH, a carboxylic acid of the formula

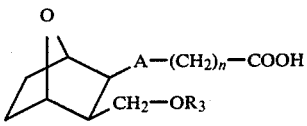

II (the preparation of which has been described in U.S. Pat. No. 4,582,854) is reacted with phosgene in the presence of a dry organic solvent, such as benzene to provide the acid chloride

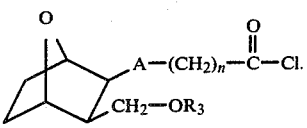

III

The acid chloride III is thereafter reacted with sodium azide in the presence of a tetraalkylammonium salt, e.g. tetrabutylammonium sulfate, in methylene chloride and water to provide the acyl azide

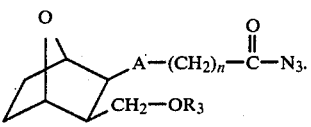

IV

Compound IV is heated to a temperature in the range of from about 50° C. to about 100° C. in the presence of an inert solvent, e.g. tetrahydrofuran or 1,2-dimethoxyethane to produce the isocyanate

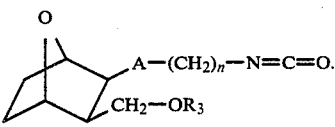

V

Compound V is then reacted with an hydroxyl amine of the of formula

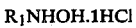

VI in the presence of triethylamine, water, and an inert solvent, e.g., tetrahydrofuran, to obtain

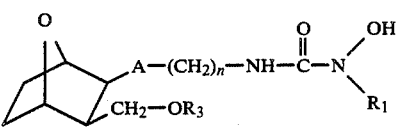

VII that is, the N-hydroxy-N-alkyl (or aryl) urea derivatives of formula I.

To make the N-hydroxy-N-alkyl (or aryl) carbamic acid derivatives of the invention, i.e. compounds of formula I wherein X=oxygen, the carboxylic acids of formula II (or their esters) are subjected to a reducing agent, such as lithium aluminum hydride, in the presence of a dry organic solvent and thereby reduced to the alcohol

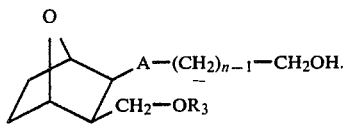

VIII

The alcohol VIII can be reacted with phosgene in the presence of triethylamine to obtain the chloroformate

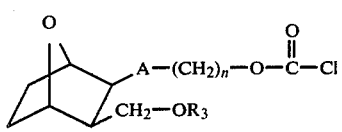

IX

Compound IX can thereafter be reacted with the desired N-alkyl- or N-arylhydroxylamine hydrochloride of formula VI in the presence of triethylamine, water and an inert organic solvent, e.g. tetrahydrofuran to provide

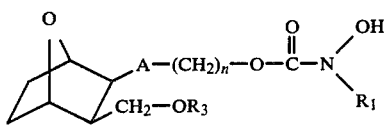

X that is, the N-hydroxy-N-alkyl (or aryl) carbamic acid derivatives of the present invention (X=oxygen).

To make the N-hydroxy-N-alkyl (or aryl) carbamothioic acid derivatives of the invention, i.e. compounds of formula I wherein X=sulfur, an alcohol of formula VIII is reacted with thiol acetic acid in the presence of triphenylphosphine, diethyldiazacarboxylate and a solvent, such as tetrahydrofuran to provide the thioacetate

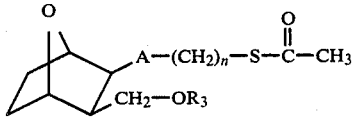

XI

Compound XI is thereafter reduced with lithium aluminum hydride in the presence of a solvent, e.g. tetrahydrofuran, to the thiol

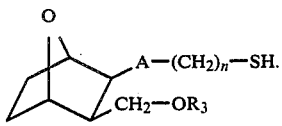

XII

Compound XII is reacted with phosgene in the presence of thriethylamine and an organIc solvent, e.g. toluene or benzene, to provide the chlorothioformate

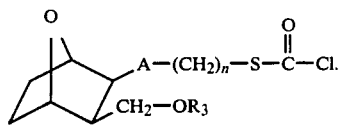

XIII

The chlorothioformate XIII can thereafter be reacted with the desired N-alkyl- or N-arylhydroxyamine hydrochloride of formula VI in the presence of triethylamine, water and an organic solvent, e.g. tetrahydrofuran, to provide

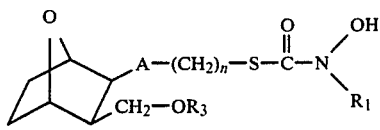

XIV that is, the N-hydroxy-N-alkyl (or aryl) carbamothioic acid derivatives of the present invention (X=sulfur).

Catalytic hydrogenations of either the acids of formula II or the alcohols of formula VIII with, for example, 5 percent palladium on carbon in the presence of methanol provide saturated compounds which can serve as starting materials for the saturated analogs of the compounds of the present invention.

The compounds of this invention have four centers of asymmetry as indicated by the asterisks in formula I. However, it will be apparent that each of the formulae set out above which do not include asterisks still represent all the possible stereoisomers thereof. All of the various stereoisomeric forms are within the scope of the present invention.

The various stereoisomeric forms of the compounds of the invention, namely, cis-endo, cis-exo and all trans forms and stereoisomeric pairs may be prepared as shown in the working Examples which follow and by employing starting materials and following the procedures as outlined in U.S.·Pat. No. 4,582,854. Examples of such stereoisomers are set out below.

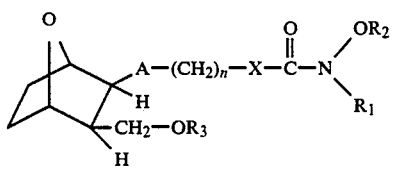

Ia (cis-exo)

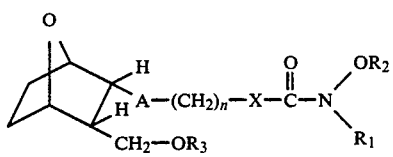

Ib (cis-endo)

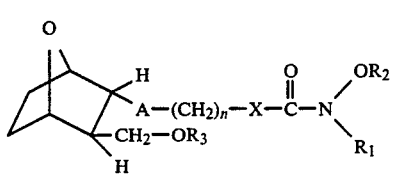

Ic (trans)

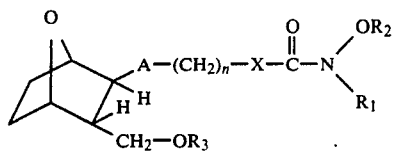

Id (trans)

The nucleus in each of the compounds of the invention is depicted as

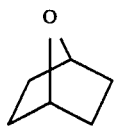

for matter of convenience; it will also be appreciated that the nucleus in the compounds of the invention may be depicted in the compounds as

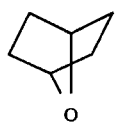

The compounds of the invention are inhibitors of the arachidonic acid enyzmes 5-lipoxygenase and cyclooxygenase and prevent formation of certain leukotriene and prostaglandins. The administration of compounds of this invention to humans or animals provides a method for treating allergy of a reagin or non-reagin nature. Asthma and psoriasis are preferably treated but any allergy or inflammation wherein leukotrienes or prostaglandins are thought to be involved as pharmacological mediators can be treated. For example, the compounds of this invention can be used for treatment of such conditions as allergic rhinitis, food allergy and urticaria, as well as asthma and psoriasis.

An effective but essentially non-toxic quantity of the compound is employed in treatment.

The compounds of the invention can be administered parenterally, orally or topically to various mammalian species known to be subject to such maladies, e.g., humans, cattle, horses, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension, lotion, cream or ointment containing about 5 to about 5000 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of the present invention.

EXAMPLE 1

[1α, 2β(3Z),3β, 4α]-N-[5-[3-[(Hexyloxy)methyl]-7-oxabicyclo [2.2.1]hept-2-yl]-3-pentenyl]-N-hydroxy-N-methylurea

A. [1α, 2β(Z),3β, 4α]-6-[[3(Hexyloxy)methyl]-7-oxabicyclo [2.2.1]hept-2-yl]-4-hexenyl chloride To a chilled and stirred solution of [1α, 2β(Z), 3β, 4α]-6-[[3-(Hexyloxy)methyl]-7-oxabicyclo[2.2.1]hept-2-yl]-4-hexenoic acid (0.9 g, 2.77 mmole; the preparation of which is described in U.S. Pat. No. 4,582,854) and dry dimethylformamide (5 drops) in dry benzene (20 ml) was added dropwise oxalyl chloride (1.8 ml, 20.6 mmole) under nitrogen. After the addition was complete, the solution was gradually warmed to room temperature and stirred for two hours. The solvent was then evaporated by a stream of nitrogen. The residue was dried in vacuo at room temperature to give the title A compound as a yellow gum (0.9 g). This compound was used immediately without further characterization.

B. [1α, 2β(Z),3β, 4α]-6-[[3-(Hexyloxy)methyl]-7-Oxabicyclo [2.2.1]hept-2-yl]-4-hexenoyl azide The acid chloride from part A (0.9 g, 2.62 mmole) and a solution of sodium azide (0.9 g, 13.84 mmole) in water (10 ml) in 20 ml of dichloromethane and tetrabutylammonium sulfate (200 mg) was stirred in an ice bath under nitrogen for one hour. The resulting mixture was extracted three times with ethyl ether. The combined ether extracts were dried over anhydrous magnesium sulfate, filtered and evaporated in vacuo to give an oil. This was passed through a column of silica gel to give 850 mg of the title B compound contaminated with a small amount of title C compound as shown by the IR spectrum.

C. [1α, 2β(Z),3β, 4α]-5-[[3-(Hexyloxy)methyl]-7-oxabicyclo [2.2.1]hept-2-yl]-3-pentenyl isocyanate A solution of the above mixture from part B (450 mg, ~1.3 mmole) in dry glyme (5 ml) was refluxed under nitrogen for 1.5 hours. The resulting solution showed a strong isocyanate peak (2275 cm$^{-1}$) and the absence of azide absorption (2150 cm$^{-1}$) in the IR spectrum. This solution was used for the reaction below without further characterization.

D. [1α, 2β(3Z),3β, 4α]-N-[5-[3-[(Hexyloxy)methyl]-7-oxabicyclo [2.2.1]hept-2-yl]-3-pentenyl]-N-hydroxy-N-methylurea To a stirred solution of N-methyl hydroxylamine hydrochloride (272.8 mg, 3.27 mmole) in a mixture of glyme (5 ml) and water (1 ml) under an atmosphere of nitrogen was added triethylamine (0.76 ml, 5.44 mmole). After a few minutes, a solution of title C compound (350 mg, 1.09 mmole) in 3.9 ml of dry glyme was added dropwise and the mixture was stirred overnight. The resulting solution was acidified with 5 percent hydrochloride acid to pH=3 and the glyme was evaporated in vacuo. The residual slurry was diluted with brine (15 ml) and extracted three times with ethyl ether. The combined ether extracts were dried over anhydrous magnesium sulfate and evaporated in vacuo to give an oil. This was chromatographed on a column of silica gel to give 155 mg of the title compound as an oil with consistent mass, IR and NMR spectral data.

EXAMPLE 2

[1R-[1α, 2β(Z), 3β, 4α]]-Hydroxymethylcarbamic acid, 5-[3-(hexyloxy)methyl]-7-oxabicyclo-[2.2.1]hept-2-yl]-3-propenyl ester

A. 1-Iodo-3-tetrahydro-2-pyranyloxy-propane

A solution of 3-iodopropanol (15 g, 80.65 mole), dihydropyran (14.7 ml, 161.29 mole) and pyridium p-toluenesulfonate (500 g, 2.0 mole) in 100 ml of dry dichloromethane was stirred at room temperature under an atmosphere of nitrogen for 2.5 hours. The resulting mixture was diluted with dichloromethane (150 ml), washed with water and saturated sodium bicarbonate solution, dried over anhydrous magnesium sulfate and evaporated in vacuo. The residue was flash-chromatographed on a silica gel column to give 20.43 g of the title A compound as an oil with a consistent NMR spectrum.

B. 1-Tetrahydro-2-pyranyloxy-3-triphenyl phosphonium iodide

A solution of compound A (20.43 g, 75.63 mmole), and triphenylphosphine (19.84 g, 75.63 mmole) in 150 ml of dry benzene was refluxed under an atmosphere of nitrogen for 24 hours. The solvent was evaporated in vacuo to give a sticky gum. This was rinsed with acetonitrile (80 ml) when a white solid precipitated out. The solid was filtered and dried over phosphorus pentoxide at 60° C. in vacuo for 20 hours to give 32.8 g of the title B compound with a consistent NMR spectrum.

C. 1-R[1α, 2β(Z),3β, 4α]-5-[[3-(Hydroxy)methyl]-7-oxabicyclo [2.2.1hept-2-yl]-1-tetrahydro-2-pyranyloxy-pent-3-ene To a chilled (−20°) and stirred slurry of title B compound (4.224 g, 9 mmole) in 40 ml of dry tetrahydrofuran was added dropwise potassium-t-amylate (4.03 ml, 1.74 M in toluene) over five minutes under an atmosphere of nitrogen. The orange solution was stirred at −20° for 2 hours and then a solution of [4aR-(4aα,5α, 8α, 8aα)]-Octahydro-5,8-epoxy-(1H)-benzopyran-3-ol (510 mg, 3 mmole) in 10 ml of dry tetrahydrofuran was added dropwise. The solution was gradually warmed up to room temperature, stirred for 18 hours and quenched with acetaldehyde (1.5 ml). After stirring at room temperature for another 30 minutes, the mixture was diluted with 30 ml of a saturated sodium bicarbonate solution and extracted three times with ethyl ether. The combined ether extracts were washed with brine, dried over anhydrous magnesium sulfate and evaporated in vacuo. The residue was flash-chromatographed on a silica gel column to give the homogeneous title C compound (810 g) as an oil with a consistent NMR spectrum.

D. 1R-[1α, 2β(Z),3β, 4α]-5-[[3-(Hexyloxy)methyl]-7-oxabicyclo [2.2.1]hept-2-yl]-1-tetrahydro-2-pyranyloxy-pent-3-ene Powdered potassium hydroxide (900 mg, 16 mmole) in 80 ml of dry xylene was refluxed under stirring in an atmosphere of nitrogen and 35–40 ml of xylene was removed by distillation. To this was added dropwise a solution of the title C compound (400 mg, 1.35 mmole) and n-hexylmesylate (1.216 g, 6.75 mmole) in 25 ml of dry xylene. The mixture was refluxed for one hour and was then cooled. Water (25 ml) was added and the solution was extracted three times with ethyl ether. The combined ether extracts were washed with brine, dried over anhydrous magnesium sulfate and evaporated in vacuo. The residue was flash chromatographed on a silica gel column to give the homogenous title D compound as an oil with a consistent NMR spectrum.

E. 1-R[1α, 2β(Z),3β, 4α]-5-[[3-(Hexyloxy)methyl]-7-oxabicyclo[2.2.1]hept-2-yl]-3-pentenol A solution of the title D compound (125 mg, 0.328 mmole) and pyridium p-toluenesulfonate (91 mg, 0.361 mmole) in 5 ml of methanol was stirred at 70° under an atmosphere of nitrogen for 1.5 hours. The methanol was mostly removed in vacuo, the residue diluted with 15 ml of water and extracted three times with ethyl ether. The combined ether extracts were washed with brine, dried over anhydrous magnesium sulfate and evaporated in vacuo. The residue was flash chromatographed on a silica gel column to give the homogeneous title E compound (85 mg) with consistent NMR spectrum.

F. 1-R[1α, 2β(Z),3β, 4α]-5-[[3-(Hexyloxy)methyl]-7-oxabicyclo[2.2.1]hept-2-yl]-3-pentenyl chloroformate To a chilled (−20°) and stirred solution of the title E compound (147.22 mg, 0.5 mmole) in a solution of phosgene in toluene (12.5%, 2 ml) was added dropwise triethylamine (70 μl, 1 mmole) under an atmosphere of nitrogen. After 15 minutes at −20°, the solution was gradually warmed up to 0° and stirred for 1.5 hours. The solvent was evaporated by a stream of nitrogen. The residue was dried in vacuo for 30 minutes to give 177.8 mg of the title F compound. This was used immediately without characterization.

G. [1R-[1α, 2β(Z),3β, 4α]]-Hydroxymethylcarbamic acid, 5-[3-[(hexyloxy)methyl]-7-oxabicyclo[2.2.1]hept-2-yl]-3-pentenyl ester To a stirred solution of N-methyl hydroxylamine hydrochloride (167 mg, 2 mmole) in a mixture of tetrahydrofuran (5 ml) and water (2 ml) was added dropwise triethylamine (0.7 ml) in an atmosphere of nitrogen. After 20 minutes, a solution of the title F compound (177.8 mg, 0.5 mmole) in tetrahydrofuran (3 ml) was added and stirred overnight. The resulting solution was acidified with 5 percent hydrochloric acid and most of the tetrahydrofuran was evaporated by a stream of nitrogen. The residual slurry was diluted with 10 ml brine and extracted three times with ethyl ether. The combined ether extracts were dried over anhydrous magnesium sulfate and evaporated in vacuo to give an oil. Another run on the same scale gave more crude product as an oil. These were combined and chromatographed on a column of silica gel to give 275 mg of the title compound as an oil, with consistent mass, IR and NMR spectral data.

EXAMPLE 3

[1R-[1α, 2β(Z),3β, 4α]]-Hydroxymethyl carbamothioic acid, 5-[3-[(hexyloxy)methyl]-7-oxabicyclo[2.2.1]hept-2-yl]-3-pentenyl ester

A. [1R-[1α, 2β(Z),3β, 4α]]-5-[3-[(Hexyloxy)methyl]-7-oxabicyclo[2.2.1]hept-2-yl]-3-penten-1-thiol, acetate ester To a chilled and stirred solution of the title E compound of Example 2 (735 mg, 2.5 mmole), triphenylphosphine (820 mg, 3.125 mmole) and thiolacetic acid (0.23 ml, 3.125 mmole) in dry tetrahydrofuran (8 ml) under an atmosphere of nitrogen was added dropwise diethyl azodicarboxylate (0.49 ml, 3.125 mmole) over five minutes. After 30 minutes at 0°, the reaction was allowed to warm to room temperature for three hours. The chromatography of an aliquot indicated that there was about 50 percent of the unreacted title E compound. Therefore, triphenyl phosphine (820 mg), thiolacetic acid (0.23 ml) and diethyl azodicarboxylate (0.49 ml) were successively added and the mixture was stirred overnight. The solvent was evaporated by a stream of nitrogen. The residue was rinsed with ethyl ether (50 ml) and filtered. The filtrate was concentrated in vacuo and flash-chromatographed on a column of silica gel to give the homogeneous title A compound (500 mg) as an oil with consistent mass, IR and NMR spectral data.

B. [1R-[1α, 2β(Z),3β, 4α]]-5-[3-[(Hexyloxy)methyl]-7-oxabicyclo[2.2.1]hept-2-yl]-3-pentene thiol To a chilled and stirred suspension of lithium aluminum hydride (78 mg, 2 mmole) in dry tetrahydrofuran (6 ml) was added a solution of title A ester (708 mg, 2 mmole) in dry tetrahydrofuran (60 ml). After one hour, 1:1 aqueous tetrahydrofuran (2 ml) was added dropwise. The mixture was stirred for an additional one-half hour, anhydrous sodium sulfate (15 g) was added and was filtered through a bed of Celite, washing the solids with small amounts of tetrahydrofuran. The combined filtrate and washings was evaporated in vacuo to afford the title compound as an oil (590 mg) with consistent mass, IR and NMR spectral data.

C. [1R[1α, 2β(Z),3β, 4α]]-Hydroxymethyl carbamothioic acid, 5-[3-[(hexyloxy)methyl]-7-oxabicyclo[2.2.1]hept-2-yl]-3-pentenyl ester By following the procedures of Example 2, F and G, except substituting the title E compound of Example 2F with [1R-[1α, 2β(Z),3β, 4α]]-5-[3-[(Hexyloxy)methyl]-7-oxabicyclo[2.2.1]hept-2-yl]-3-pentene thiol, the title compound can be obtained.

EXAMPLES 4 to 28

The following additional compounds within the scope of the present invention may be prepared by employing the teachings as outlined above and in the working Examples.

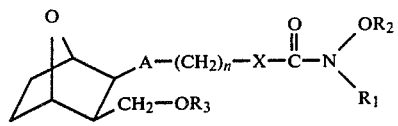

| Ex. No. | R₁ | R₂ | R₃ | X | A | n |
|---|---|---|---|---|---|---|
| 4 | $C_2H_5$ | $CH_3$ | $C_6H_{13}$ | NH | $CH_2-CH=CH-$ | 1 |
| 5 | $C_3H_7$ | $C_2H_5$ | $C_6H_{13}$ | NH | $CH_2-CH=CH-$ | 1 |
| 6 | $C_4H_9$ | $C_4H_9-$ | $-CH_2-CH=CH-CH_3$ | S | $CH_2-CH=CH-$ | 4 |
| 7 | $C_5H_{11}$ | $-CH_2-C_6H_5$ | $-CH_2-CH=CH-CH_3$ | S | — | 6 |
| 8 | $-C_6H_4-CH_3$ | H | $-CH_2-C\equiv C-CH_3$ | O | — | 5 |
| 9 | $-C_6H_4-CH_3$ | H | $-CH_2-C\equiv C-CH_3$ | NH | $-CH_2-CH=CH-$ | 3 |
| 10 | $-CH_2-C_6H_5$ | $\overset{O}{\underset{\|}{C}}-CH_2-CH_2-CH_3$ | $C_5H_{11}$ | O | $-CH_2-CH=CH-$ | 2 |
| 11 | $-CH_2-C_6H_5$ | $\overset{O}{\underset{\|}{C}}-C_6H_5$ | $C_4H_9$ | O | $-CH_2-CH=CH-$ | 2 |
| 12 | $C_6H_{13}$ | H | $C_3H_7$ | O | $-CH_2-CH=CH-$ | 3 |
| 13 | $C_7H_{15}$ | $\overset{O}{\underset{\|}{C}}-CH_2-CH_3$ | $C_2H_5$ | S | $-CH_2-CH=CH-$ | 4 |
| 14 | $C_8H_{17}$ | $\overset{O}{\underset{\|}{C}}-C_6H_5$ | $CH_3$ | S | — | 7 |
| 15 | $-CH_2-CH=CH-CH_3$ | $C_2H_5$ | $C_5H_{11}$ | NH | $-CH_2-CH=CH-$ | 4 |
| 16 | H | H | $-CH_2-CH=CH-CH_2-CH_3$ | S | $-CH_2-CH=CH-$ | 8 |
| 17 | $-C_6H_4-CH_3$ | H | $-CH_2-C\equiv C-CH_3$ | NH | $-CH_2-CH=CH-$ | 4 |
| 18 | $-C_6H_4-CH_3$ | $-CH_2-C_6H_5$ | $C_2H_5$ | O | $-CH_2-CH=CH-$ | 5 |
| 19 | $-C_6H_4-CH_3$ | $\overset{O}{\underset{\|}{C}}-CH_2-CH_2-CH_2-CH_3$ | $-CH_3$ | NH | $-CH_2-CH=CH-$ | 3 |
| 20 | $-C_2H_5$ | $-CH_2-CH_2-\overset{O}{\underset{\|}{C}}-CH_3$ | $-C_2H_5$ | NH | $-CH_2-CH=CH-$ | 2 |

-continued

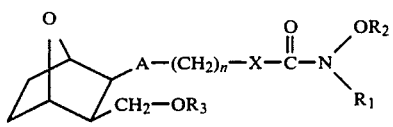

| Ex. No. | R₁ | R₂ | R₃ | X | A | n |
|---|---|---|---|---|---|---|
| 21 | $C_3H_7$ | ![benzoyl] −C(=O)−C₆H₅ | $C_8H_{17}$ | S | — | 2 |
| 22 | $-CH_3$ | H | $C_7H_{15}$ | S | — | 3 |
| 23 | $-CH_3$ | $C_3H_7$ | $C_3H_7$ | O | $-CH_2-CH=CH-$ | 4 |
| 24 | $-CH_2-C_6H_5$ | $C_2H_5$ | $-CH_2-CH=CH-CH_3$ | NH | $-CH_2-CH=CH-$ | 3 |
| 25 | $-CH_2-C_6H_5$ | $C_3H_7$ | $-CH_3$ | S | $-CH_2-CH=CH-$ | 2 |
| 26 | $-CH_2-C_6H_5$ | $CH_3$ | $-C_6H_{13}$ | S | $-CH_2-CH=CH-$ | 3 |
| 27 | $-C_2H_5$ | H | $-C_6H_{13}$ | O | $-CH_2-CH=CH-$ | 4 |
| 28 | $-CH_3$ | H | $-C_6H_{13}$ | O | $-CH_2-CH=CH-$ | 5 |

What is claimed is:

1. A compound of the formula

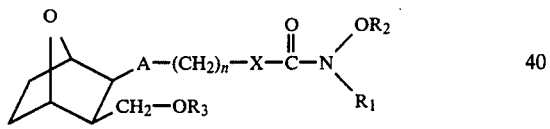

wherein $R_1$ is hydrogen, lower alkyl, alkenyl, aryl or aralkyl; $R_2$ is hydrogen, lower alkyl, aralkyl, alkanoyl or aroyl; $R_3$ is lower alkyl, alkenyl or alkynyl; A is $-CH_2-CH=CH-$ or a single bond; X is oxygen, sulfur or NH; n is an integer from 1 to 8; and all stereoisomers thereof; wherein the term lower alkyl or alkyl refers to straight and branched chain radicals of up to 12 carbons, as well as such groups including a halo-substituent, an alkoxy substituent, an aryl substituent, an aralkyl substituent, a haloaryl substituent, a cycloalkyl substituent, an alkylcycloalkyl substituent, hydroxy, an alkylamino or dialkylamino substituent, an alkanoylamino substituent, an arylcarbonylamino substituent, a nitro substituent, a cyano substituent, a thiol substituent or an alkylthio substituent;

the term alkenyl refers to an unsaturated hydrocarbon group having from 2 to 8 carbons and a single carbon-carbon double bond;

the term alkynyl refers to an unsaturated hydrocarbon group having from 2 to 8 carbons and a single carbon-carbon triple bond;

the term aryl by itself, or as a part of aralkyl or aroyl, refers to monocyclic or bicyclic aromatic groups containing from 6 to 10 carbons in the ring portion, selected from phenyl, naphtyl, substituted phenyl or substituted naphtyl wherein the substituent on either the phenyl or naphthyl may be 1 or 2 lower alkyl groups, 1 or 2 halogens selected from CL, Br or F, 1 or 2 lower alkoxy groups, 1 or 2 hydroxyl groups, 1 or 2 alkylamino or dialkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups;

the term aralkyl or aryl-alkyl refers to said alkyl groups substituted with one of said aryl groups;

the term alkanoyl refers to a group comprising a carbonyl and one of said alkyl groups; and, the term aroyl refers to a group comprising a carbonyl and one of said aryl groups.

2. A compound of claim 1 wherein $R_1$ and $R_3$ are each the same, or a different, alkyl, $R_2$ is hydrogen, A is $-CH_2-CH=CH-$, n=2, and X is NH.

3. A compound of claim 1 wherein $R_1$ and $R_3$ are each the same, or a different, alkyl, $R_2$ is hydrogen, A is $-CH_2-CH=CH-$, n=2, and X is oxygen.

4. A compound of claim 1 wherein $R_1$ and $R_3$ are each the same, or a different, alkyl, $R_2$ is hydrogen, A is $-CH_2-CH=CH-$, n=2, and X is sulfur.

5. A compound of claim 1 having the name [1α, 2β(3Z),3β, 4α]-N-[5-[3-[(Hexyloxy)methyl]-7-oxabicyclo[2.2.1]hept-2-yl]-3-pentenyl]-N-hydroxy-N-methylurea.

6. A compound of claim 1 having the name [1R-[1α, 2β(Z),3β, 4α]]-Hydroxymethylcarbamic acid, 5-[3-[(hexyloxy)methyl]-7-oxabicyclo[2.2.1]hept-2-yl]-3-pentenyl ester.

7. A compound of claim 1 having the name [1R-[1α, 2β(Z),3β, 4α]]-Hydroxymethyl carbamothioic acid, 5-[3-[(hexyloxy)methyl]-7-oxabicyclo[2.2.1]hept-2-yl]-3-pentenyl ester.

8. A composition for inhibiting allergic conditions in a mammalian species comprising an effective amount of a compound as defined in claim 1 or a pharmaceutically acceptable salt thereof and a pharmaceutically acceptable carrier therefor.

9. A method of simultaneously inhibiting arachidonic acid cyclooxygenase and arachidonic acid 5-lipoxygenase which comprises administering to the circulatory system of a mammalian host an effective amount of a compound as defined in claim 1 or a pharmaceutically acceptable salt thereof.

10. The method of claim 9 wherein said compound is administered in an amount within the range of from about 1 to about 100 mg/kg.

11. A method for treating asthma in a mammalian species in need of such treatment, which comprises administering to a mammalian host an effective amount of a compound as defined in claim 1 or a pharmaceutically acceptable salt thereof.

12. A method of treating psoriasis in a mammalian species in need of such treatment which comprises administering to a mammalian host an effective amount of a compound as defined in claim 1 or a pharmaceutically acceptable salt thereof.

* * * * *